United States Patent [19]

Zollingger et al.

[11] Patent Number: 5,398,560
[45] Date of Patent: Mar. 21, 1995

[54] APPARATUS FOR INSPECTING PIPING

[75] Inventors: W. Thor Zollingger, Martinez, Ga.;
D. Keith Appel, Aiken, S.C.; Larry R. Park, Raleigh, N.C.

[73] Assignee: The United States of America as represented by the United States Department of Energy, Washington, D.C.

[21] Appl. No.: 89,679

[22] Filed: Jul. 12, 1993

[51] Int. Cl.⁶ .................. G01M 19/00; G01N 27/82; G01N 29/04; G21C 17/017
[52] U.S. Cl. .................. 73/865.8; 73/866.5; 73/623; 324/220; 376/249
[58] Field of Search .............. 73/865.8, 866.5, 432.1, 73/623, 638; 324/200, 220, 221, 226, 228; 376/245, 249; 174/136, 137 R, 137 A, 137 B; 254/134.3 FT

[56] References Cited

U.S. PATENT DOCUMENTS

| 3,596,512 | 8/1971 | Bixby | 73/170.28 |
|---|---|---|---|
| 3,786,684 | 1/1974 | Wiers et al. | 324/220 |
| 3,916,302 | 10/1975 | Madewell | 324/220 |
| 4,044,292 | 8/1977 | Tomlin | 320/2 |
| 4,195,529 | 4/1980 | Madoian et al. | 73/638 |
| 4,361,044 | 11/1982 | Kupperman et al. | 73/623 |
| 4,372,161 | 2/1983 | de Buda et al. | 73/866.5 X |
| 4,413,231 | 11/1983 | Amdero et al. | 324/220 |
| 4,708,136 | 11/1987 | Saito | 128/303.1 |
| 4,754,328 | 6/1988 | Barath et al. | 358/98 |
| 4,807,484 | 2/1989 | Goedecke | 73/865.8 |
| 4,841,988 | 6/1989 | Fetter et al. | 128/804 |
| 4,926,518 | 5/1990 | Mikol | 15/104.33 |
| 4,952,875 | 8/1990 | Adams et al. | 324/220 |
| 5,023,549 | 6/1991 | Dau et al. | 324/220 |
| 5,174,164 | 12/1992 | Wilheim | 73/866.5 |
| 5,176,401 | 1/1993 | Chapman | 280/775 |
| 5,254,117 | 10/1993 | Rigby et al. | 606/46 |
| 5,303,605 | 4/1994 | Douglass | 74/368 |

FOREIGN PATENT DOCUMENTS

| 2837488 | 12/1979 | Germany | 324/220 |
|---|---|---|---|
| 1488833 | 10/1977 | United Kingdom | 324/220 |

Primary Examiner—Hezron E. Williams
Assistant Examiner—Daniel S. Larkin
Attorney, Agent, or Firm—Brian R. Tumm; Harold M. Dixon; William R. Moser

[57] ABSTRACT

An inspection rabbit for inspecting piping systems having severe bends therein. The rabbit consists of a flexible, modular body containing a miniaturized eddy current inspection probe, a self-contained power supply for proper operation of the rabbit, an outer surface that allows ease of movement through piping systems and means for transmitting data generated by the inspection device. The body is preferably made of flexible polyvinyl chloride (PVC) tubing or, alternatively, silicone rubber with a shrink wrapping of polytetrafluoroethylene (TEFLON ®). The body is formed to contain the power supply, preferably a plurality of batteries, and a spool of communication wire that connects to a data processing computer external to the piping system.

17 Claims, 3 Drawing Sheets

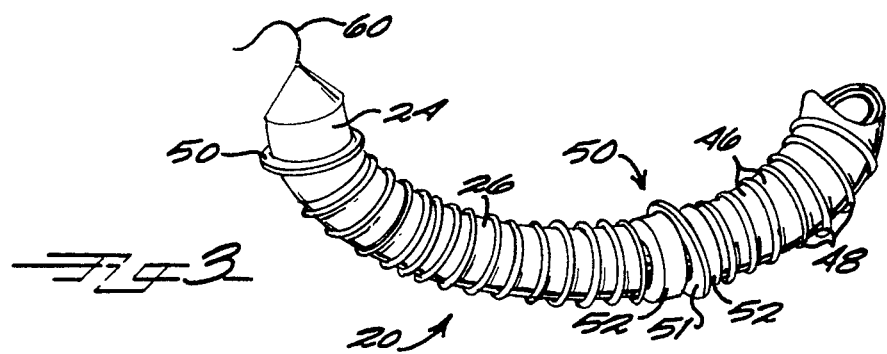
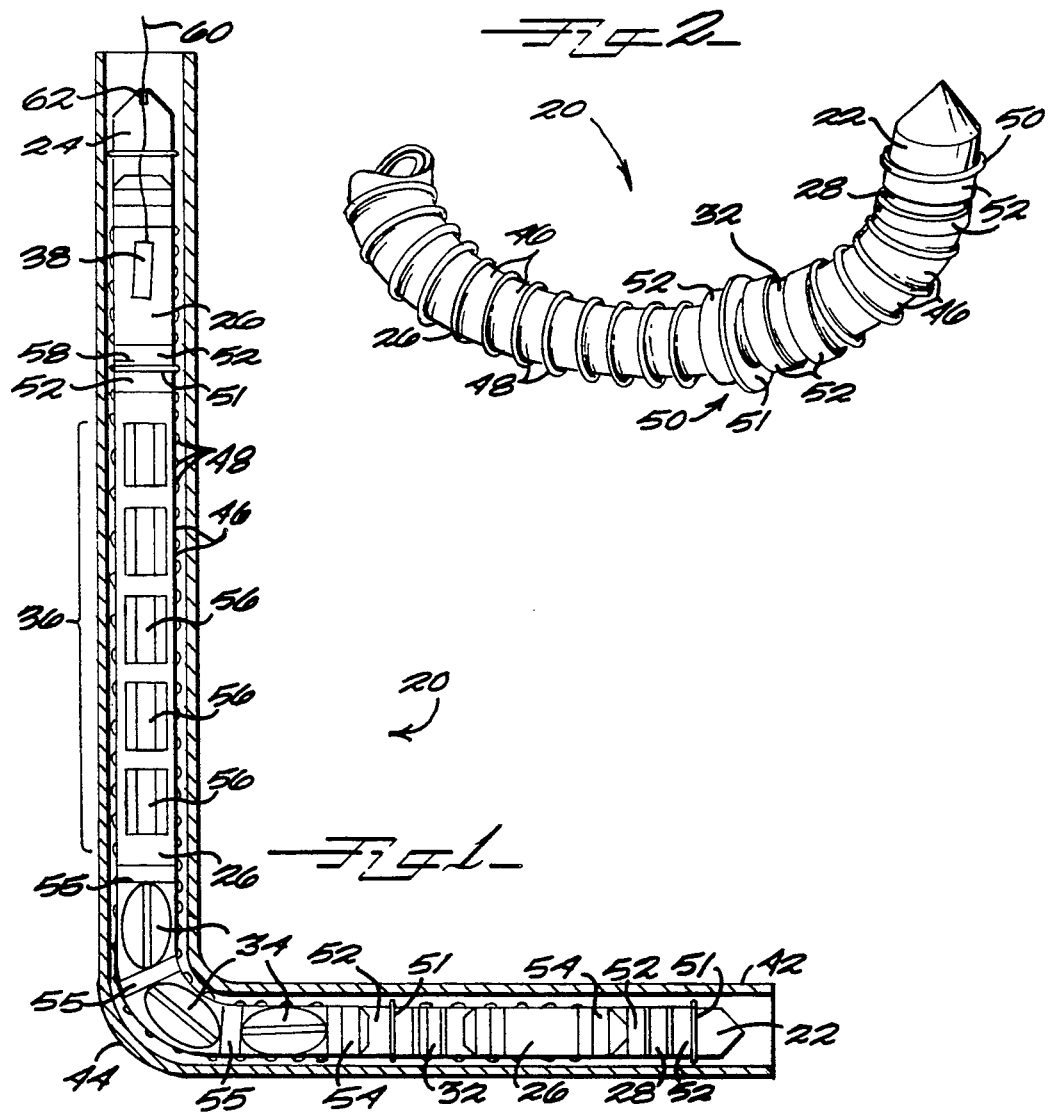

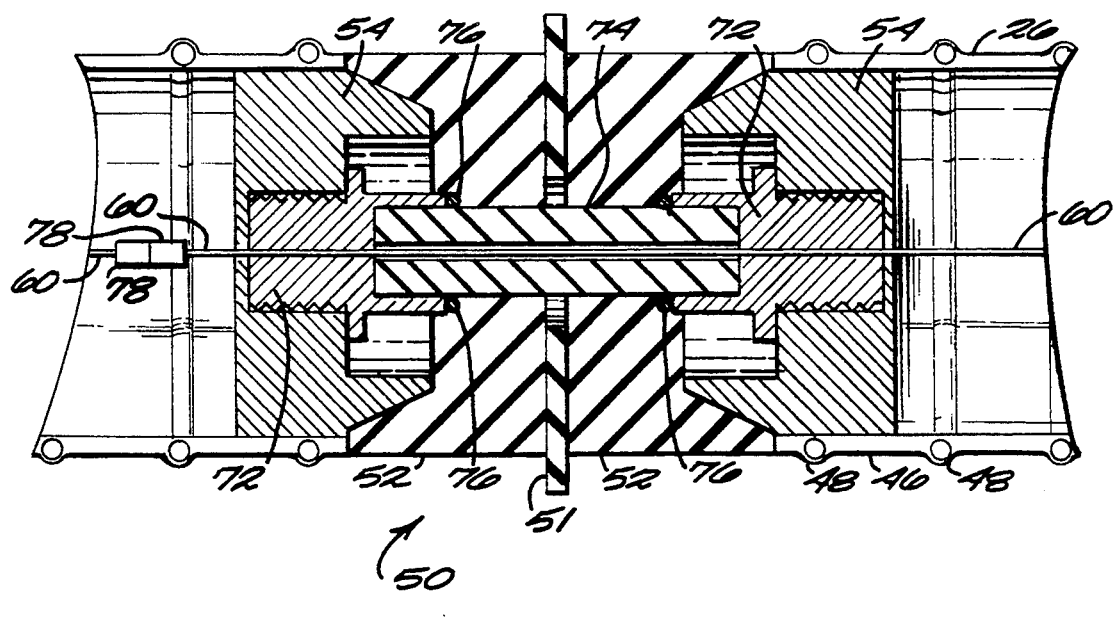

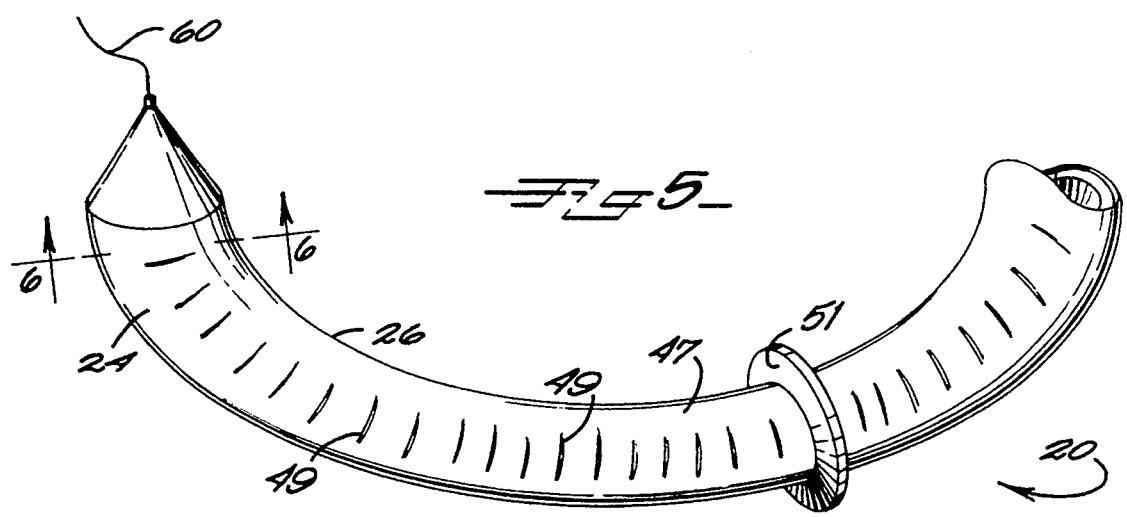
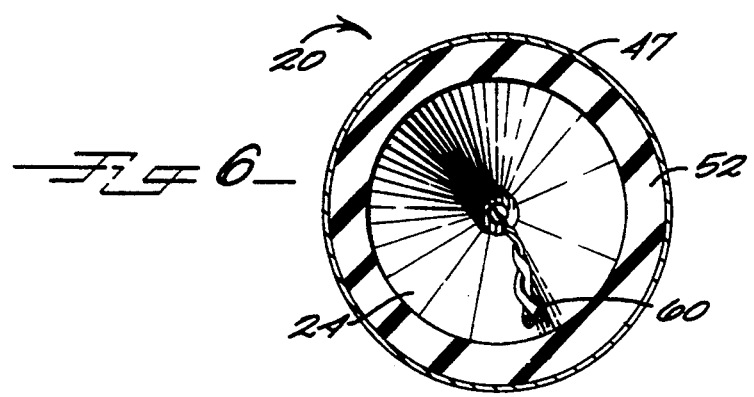

APPARATUS FOR INSPECTING PIPING

The United States Government has rights in this invention pursuant to Contract No. DE-AC09-89SR18035 between the U.S. Department of Energy and Westinghouse Savannah River Company.

BACKGROUND OF THE INVENTION

1. Field of the Invention

The present invention relates to devices for pipe inspecting. More particularly, the present invention relates to inspection devices, carrying inspection probes (sometimes called "rabbits"), that have sufficient flexibility to negotiate bends in piping systems.

2. Discussion of Background

Cleaning, inspecting and testing are widely known in the construction and maintenance of piping systems. Devices carrying testing and inspection probes, or "rabbits", are used to move these probes through piping systems so that they can survey surfaces of piping and look for damaged or flawed structural features. Typically, such inspection devices comprise a testing probe, such as an eddy current probe, contained within a rabbit support structure that travels through the piping system being inspected.

Several U.S. Pat. Nos. disclose devices carrying eddy current testing probes, including 5,023,549 issued to Dau et al, 4,952,875 issued to Adams et al, 3,916,302 issued to Madewell and 4,413,231, issued to Amedro et al.

To be effective, testing and inspection devices must be dimensioned to pass through various sized pipes and designed to negotiate piping bends easily. Therefore, the relative size and flexibility of a particular inspection device is often crucial.

There have been a number of attempts to design flexible rabbits for pipe inspection. Dau et al (5,023,549) feature an expandable elastic membrane for supporting an eddy current sensor to be used in nuclear plant piping. The flexible membrane is made of rubber, plastic or a similar material.

Adams et al (4,952,875) disclose an eddy current testing device for U-shaped tubes in a heat exchanger. The device includes a plurality of elastic hoses separated by coils, a local recognition unit and an elastic insertion tip at the front end. Similarly, Amedro et al (4,413,231) have an insertion tip, a measuring head, a probe body and connecting members.

Many pipe inspection devices are modular in configuration in order to enhance their flexibility. For instance, deBuda et al (4,372,161) and Madoian et al (4,195,529) both disclose pneumatically operated, modular units that move through piping. DeBuda et al ('161) feature an elongate cylindrical tube of flexible resilient material, partitioned by longitudinally spaced plugs which are hermetically sealed to the wall of the tube to form a series of chambers. Madoian et al ('529) use chambers surrounded by elastic sleeves and interconnected by a flexible bellows to move probes of a flaw detection system through piping.

Another patent, U.S. Pat. No. 5,174,164, issued to Wilheim, discloses a flexible cable for carrying an inspection probe through tubing. The cable comprises a core with a plurality of adjacent, interconnecting beads surrounding and disposed along the exterior. Each pair of adjacent beads defines a ball and socket joint for allowing the cable to flex as it is moved in the tubing.

Although many devices for inspecting piping are currently known and available, there exists a need for an pipe inspection device made to pass easily through piping and having the requisite flexibility to negotiate severe bends in the piping system being inspected.

SUMMARY OF THE INVENTION

According to its major aspects and broadly stated, the present invention is a device for inspecting piping systems. In particular, it is a rabbit for inspecting piping systems in which the piping system has bends and elbows. The rabbit consists of a flexible, modular body containing a miniaturized eddy current inspection probe, a power supply, an outer surface that facilitates movement through piping systems and means for transmitting data generated by the probe. The body is preferably made of flexible polyvinyl chloride (PVC) tubing or, alternatively, silicone rubber covered with a shrink wrapping of polytetrafluoroethylene (available under the trademark TEFLON ®). The body is formed to carry its own power supply, preferably a plurality of batteries, and a spool of electrical communication wire that connects to a data processing computer external to the piping system. The rabbit is used preferably with launching systems that move the rabbit through the piping by fluid pressure.

A major feature of the present invention is the seal configuration of each joint of the rabbit. The seal configuration is a molded silicone rubber joint that supports and seals against a urethane rubber disk seal. The disk seal provides the motive force that pushes the rabbit through the piping. The silicone provides support for the thin disk, provides a flexible sealing surface to the disk and allows the particular rabbit joint to flex while negotiating tight corners. There is sufficient flexibility and clearance from the outer surface of the molded silicone to the pipe wall to allow the disk seal to fold back as it passes over $\frac{1}{8}''$ weld bends that protrude into the piping.

Another major feature of the present invention is the rabbit body. The rabbit body is preferably made of polyvinyl chloride (PVC) tubing having a plurality of low friction ribs and joints made of silicone rubber. Alternatively, the rabbit body can be made entirely of silicone rubber and covered with a shrink wrapping of polytetrafluoroethylene. The advantage of this feature is that the body is easily—and resiliently—deformable and "slippery" to allow the inspection rabbit to pass more easily through piping systems while still maintaining the shape of the rabbit.

Another feature of the present invention is the communication wire spool contained in the rabbit body. The spool plays out communication wire from the rabbit as needed when the rabbit travels through a piping system. The communication wire is in electrical connection from the rabbit's detection probe to a data storage and processing computer located external to the piping system. This feature allows continuous electrical communication to be maintained between the rabbit's detection probe and the external computer system.

Still another feature of the present invention is the power source contained within the inspection rabbit. The body of the rabbit has means formed therein for holding a power source, preferably a plurality of rechargeable AA batteries positioned in series. This feature eliminates the need for external power with the attendant wiring to the inspection rabbit that limits the mobility of the rabbit as it moves through a piping system.

Another related feature of the present invention is the inspection rabbit's external, battery recharge connection. This feature allows the batteries contained in the body of the rabbit to be recharged without removing the batteries from the body of the rabbit.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 1 is a cross-sectional view of an inspection device according to a preferred embodiment of the present invention;

FIG. 2 is a perspective view of the head portion of the inspection device of FIG. 1;

FIG. 3 is a perspective view of the tail portion of the inspection device of FIG. 1;

FIG. 4 is a side cross-sectional view of a removable joint segment located in the tail portion of the device of FIG. 1;

FIG. 5 is a perspective view of the tail portion of the inspection device of FIG. 1 according to an alternative embodiment of the present invention; and FIG. 6 is a cross-section of the inspection probe of FIG. 5 taken along the lines 6—6.

DETAILED DESCRIPTION OF A PREFERRED EMBODIMENT

In the following description similar components are referred to by the same reference numeral in order to simplify the understanding of the sequential aspect of the drawings.

Referring now to FIG. 1, the inspection rabbit 20 in its preferred embodiment is a slender, flexible body having a head or nose 22 at one end, a tail 24 at the opposite end and a plurality of body modules 26 therebetween. Body modules 26, which are flexibly connected to each other and to nose 22 and tail 24, contain an inspection driver coil 28, an inspection detector coil 32, a plurality of electronic inspection packages 34, a self-contained power supply (shown generally as 36) and a communication wire spool 38.

Rabbit 20 is used to inspect a pipe 42, which is preferably a portion of a piping system with very small diameters (approximately 2") and one or more severe bends 44. Rabbit 20 is moved through piping 42 by any suitable means, preferably by pushing-pulling rabbit 20 with a positive displacement pump in a closed loop. The capabilities of such a positive displacement pump allow rabbit 20 to be moved controllably in either direction within piping 42.

Both nose 22 and tail 24 of rabbit 20 are preferably made of a compressible yet resilient material, such as silicone rubber. Body modules 26 are preferably made of ribbed polyvinyl chloride (PVC) flexible tubing 46, as shown also in FIGS. 2–3, or, alternatively, molded from tear-resistant, flexible silicone rubber.

PVC tubing 46 has a plurality of low-friction outer ribs 48 that assist rabbit 20 in negotiating bends 44 in piping 42. Also, the use of PVC tubing 46 allows rabbit 20 to be assembled more easily than body modules 26 made of molded silicone rubber, since PVC adapters (discussed below) can be glued directly to the tubing.

Using body modules 26 made of a flexible yet resilient material lo like PVC tubing 46 prevents rabbit 20 from becoming lodged within pipe 42 on weld crowns (not shown) or other obstacles within pipe 42. Also, the resiliency of nose 22 and tail 24 allows rabbit 20 to negotiate bends 44 or elbows in piping 42. If nose 22 and tail 24 of rabbit 20 were made of hard, non-resilient materials, nose 22 and tail 24 would not deform as needed in passing through obstructions in the wall of piping 42.

Alternatively, body modules 26 can be made of molded silicon rubber, similar to head 22 and tail 24. However, although molded silicone rubber has the necessary resilience, the high coefficient of friction of the rubber could cause rabbit 20 to get stuck in piping bends 44. Therefore, body modules 26 made of silicone rubber would be jacketed with a slick coating (shown as 47 in FIGS. 5–6), preferably polytetrafluoroethylene (sold under the trademark TEFLON ®).

In this alternative embodiment, the TEFLON ® coating is preferably applied by shrink wrapping it onto body modules 26. Shrink wrapping means any process that causes a thin layer of a material to conform to the outside contours of a body. Typically, a sleeve of a material is fitted over the underlying body and then, upon the application of heat, the material shrinks. As it shrinks, it conformed closely to the contours of the body.

In this embodiment, a thin sleeve of TEFLON ® or other suitable material is placed around body modules 26 and sufficient heat, vacuum pressure or other means is applied so that the TEFLON ® layer conforms or shrink-fits around and encases body modules 26. In order to provide for flexibility while maintaining slipperiness of rabbit 20, the TEFLON ® coating can be slit radially (shown as 49 in FIG. 5), or alternatively, cut into annular sections.

A plurality of polyurethane seal sections 50 are molded into body modules 26 at their ends to connect body modules 26 correspondingly with nose 22, tail 24 or other body modules 26 in a manner that maintains the flexibility and resiliency of rabbit 20. Initially, polyurethane seal sections 50 comprise a fiat, annular polyurethane seal 51 having a center hole, preferably 1" in diameter, but are connected correspondingly by molding portions of silicone rubber 52 through an adapter 54 (shown in FIGS. 1, 4) into the inside of body modules 26. Silicone rubber portions 52 are also molded through the center of polyurethane seals 51.

Silicone rubber portions 52 do not pull through the smaller inside diameter of adapter 54, but do pull away from polyurethane seals 50, as shown in FIGS. 2–3, thus allowing rabbit 20 to flex easily at the locations of polyurethane seals 51.

In the same manner as just described, polyurethane seal sections 50 connect nose 22 and tail 24 to corresponding body modules 26. Similarly, the silicone rubber pulls away from polyurethane seals 51, thus allowing rabbit 20 to flex easily at respective seal locations.

Polyurethane seals 51 deform by folding back as rabbit 20 goes over any weld crowns or other obstacles inside piping 42. Typically, weld crowns protrude as much as $\frac{1}{8}$" and other seal types and seals made of most materials will not deform sufficiently to pass over the weld crowns. Such seals are normally thicker and less supported than polyurethane seals 51 and have a tendency to fold and skew, which tends to interfere with the flow that pushes rabbit 20 along the interior of piping 42. Thus, rubber portions 52 are molded around polyurethane seals 51 to prevent such folding.

Driver coil 28, detector coil 32 and electronic packages 34 comprise the eddy current detection equipment, which has been miniaturized to be mountable within rabbit 20. Preferably, driver coil 28 is molded into the silicone rubber of nose 22 and is shrink wrapped in TEFLON ® shrink tubing for protection and low friction.

Detector coil 32 is also molded into the silicone rubber near one of polyurethane seals 51 connecting body modules 26 near head 22. Driver coil 28 and detector coil 32 must be positioned within a predetermined distance in order to operate properly. Thus, depending on the relative sizes of body module 26, driver coil 28 and detector coil 32 may or may not have to be molded into opposing ends of one module of body module 26.

As is known in the art, detector coil 32 can take on any number of coil arrangements. Also, similar to driver coil 28, detector coil 32 is shrink-wrapped in TEFLON ® tubing for protection and reduction of friction.

Electronics inspection packages 34 are likewise formed within one of body modules 26. Each package of electronics inspection packages 34 preferably contains one or more circuit boards embedded in a non-conductive buffer material, which is then placed into one of body modules 26. Again, depending on the relative size of each module of body module 26, one or more electronics packages 34 may be placed within the same body module 26. Electronics inspection packages 34 are used to process electronic information derived from driver coil 28 and detector coil 32. Also, electronics inspection packages 34 may be separated by, and partially secured within body module 26 by, a plurality of silicone spacers 55.

Power supply 36 preferably comprises a plurality of rechargeable AA batteries 56. Batteries 56 are arranged to be wired in series, preferably five groups of 4-battery packages electrically connected in series. Batteries 56 are waterproofed prior to placement within body module 26. Thus, batteries 56 can be molded into silicone rubber or other suitable material for secure placement within body modules 26. A stiff wire spine can be added down the center of rabbit 20 to prevent compression of electronics inspection packages 34 and batteries 56, which tends to short out the circuits within electronics inspection packages 34.

Preferably, rabbit 20 has an external charging connection 58 (shown in FIG. 1) disposed between one of silicon rubber portions 52 and one of polyurethane seals 51 near tail 24 and in electrical connection with batteries 56. External charging connection 58 allows batteries 56 to be charged without removing batteries 56 from their respective body module 26.

Thus, batteries 56 can be recharged between uses of rabbit 20 or while rabbit 20 is waiting to be deployed within piping 42, such as within the launch tube of a rabbit launching system (not shown). A charging circuit (not shown) in electrical connection with external charging connection 58 can be configured so that it switches off automatically when the electrical isolation of external charging connection 58 is broken as the rabbit is launched into piping 42.

Communication wire spool 38 is contained within one of body modules 26, preferably near tail 24. Spool 38 holds a predetermined amount of very fine, twisted, communication wire 60, preferably having a length of approximately 1000 feet. Communication wire 60 is played out of the back of the spool 38 through a tube 62 located through the center of tail 24 as rabbit 20 travels down the piping 42. Spool 38 has a plastic case (not shown) that can be opened by removing its cap so that expendable communication wire 60 can be replaced for the next run by rabbit 20. Preferably, the rear section of rabbit 20 is easily removable to make spool replacements quick and simple.

Communication wire 60 passes through the center of polyurethane seal sections 50 through the inside diameter of adapter 54 and polyurethane seal 51 and are molded into silicone rubber portions 52. Also, communication wire 60 being played out through tube 62 of tail 24 is in electrical communication with a data storage and processing computer (not shown) located external to piping 42. Thus, electrical communication can be maintained between rabbit 20 and the external computer while allowing rabbit 20 to travel through piping 42. Because of the fineness of the communication wire 60, rabbit 20 can travel around bends 44 in piping 42 without having communication wire 60 interfere with the movement of rabbit 20.

Referring now to FIG. 4, one of polyurethane seal sections 50 near tail 24 is preferably adapted to be removable so that tail 24 and the body module 26 nearest tail 24 can be removed from rabbit 20. In this particular seal section, both adapters 54 have a male tubing quick connect 72 attached therein. Quick connects 72 are preferably ⅜" tubing quick connects.

Coinciding with quick connects 72 is a section of rubber or plastic tubing 74, preferably ⅜" tubing, that connects to each quick connect 72 in the manner shown in FIG. 4. Tubing 74 holds body modules 26 together and provides a pass-through for communication wire 60. Tubing 74 is released from quick connects 72 by depressing a connector collet 76 attached to each quick connect 72. Also, communication wire 60 is connected by a wire connector 78 so that communication wire 60 can be disconnected near polyurethane seal section 50 when body modules 26 are separated.

Alternatively, other methods of communication between rabbit 20 and the external computer can be used, such as fiber optic cable, RF broadcasting using piping 42 as an antenna, or using ultrasonic sound to send data information through the fluid within piping 42. Accordingly, other equipment can be carried on the rabbit 20, including ultrasonic inspection probes, video cameras, radiation level probes, or other types of devices.

In use, communication wire 60 from spool 38 is connected to the data storage and processing computer (not shown) so that electrical connection is established between electronics inspection packages 34 in rabbit 20 and the eternally located computer. Rabbit 20 is then positioned within piping 42 by any suitable means, preferably by an appropriate rabbit launching system.

Rabbit 20 is moved through piping 42 to inspect the walls of piping 42 for flaws. Alternatively, rabbit 20 may be carrying other equipment to perform different services, such as cleaning and the like.

When rabbit 20 is in operation, driver coil 28 creates a magnetic field that permeates through piping 42. Detector coil 32 picks up disturbances in this magnetic field that indicate flaws in piping 42. The information detected from detector coil 32 is processed within rabbit 20 by the first two of preferably three electronics inspection packages 34 and multiplexed in the third of preferably three electronics inspection packages 34 to be sent back to the data storage and processing computer.

It will be apparent to those skilled in the art that many changes and substitutions can be made to the preferred embodiment herein described without departing from the spirit and scope of the present invention as defined by the appended claims.

What is claimed is:

1. Apparatus for inspecting piping, said apparatus comprising:
   a body having an axis, said body made of a resilient material, said resilient material having a first coefficient of friction with respect to said piping;
   an inspection instrument carded by said body for measuring a characteristic of said piping and generating data related to said characteristic; and
   a flexible outer surface covering said body, said outer surface made of a material selected from the group consisting of polytetrafluoroethylene and polyvinyl chloride, said outer surface having a second coefficient of friction with respect to said piping, said second coefficient of friction being less than said first coefficient of friction so that said outer surface enables said apparatus to slip through said piping.

2. The apparatus as recited in claim 1, wherein said outer surface further comprises a flexible tube having a plurality of ribs formed thereon for increasing the flexibility of said body transverse to said axis so that said apparatus can pass through bends in said piping.

3. The apparatus as recited in claim 1, wherein said piping has an interior with obstacles extending therefrom and wherein said resilient material allows said apparatus to pass by said obstacles when said apparatus moves through said piping.

4. The apparatus as recited in claim 1, further comprising means carried by said body for supplying power to said inspection instrument.

5. The apparatus as recited in claim 1, further comprising means in electrical connection with said inspection instrument for transmitting said data from said inspection instrument.

6. The apparatus as recited in claim 1, wherein said body is made of silicone rubber.

7. Apparatus for inspecting piping, said apparatus comprising:
   a body having an axis, said body made of a resilient material;
   an inspection instrument carried by said body for measuring a characteristic of said piping and generating data related to said characteristic;
   a flexible outer surface covering said body and said inspection instrument;
   at least one rechargeable battery carded within said body for supplying power to said inspection instrument; and
   means formed in said body for allowing said at least one rechargeable battery to be recharged without removing said at least one rechargeable battery from said body.

8. The apparatus as recited in claim 7, further comprising means in electrical connection with said inspection instrument for transmitting data from said inspection instrument.

9. The apparatus as recited in claim 7, further comprising an outer surface covering said body, said outer surface having a plurality of radial slits formed therein for increasing the flexibility of said body transverse to said axis.

10. The apparatus as recited in claim 7, wherein said outer surface further comprises a flexible tube having a plurality of ribs formed thereon for increasing the flexibility of said body transverse to said axis so that said apparatus can pass through bends in said piping.

11. The apparatus as recited in claim 7, wherein said outer surface is made of a material selected from the group consisting of polyvinyl chloride and polytetrafluoroethylene.

12. Apparatus for inspecting piping, said apparatus comprising:
   a body having an axis, said body made of a resilient material;
   an inspection instrument carried by said body for measuring a characteristic of said piping and generating data related to said characteristic;
   a flexible outer surface covering said body and said inspection instrument; and
   means in electrical connection with said inspection instrument for transmitting said data from said inspection instrument, said transmitting means playing out electrical wire from said apparatus as said body moves through said piping.

13. The apparatus as recited in claim 12, wherein said body has a front end and a rear end, wherein said transmitting means further comprises electrical wire, and wherein said apparatus further comprises a spool wire case carried by said body so that said electrical wire plays out from said apparatus as said body moves through said piping.

14. The apparatus as recited in claim 12, wherein said outer surface is made of a flexible tube having a plurality of ribs formed thereon for increasing the flexibility of said body transverse to said axis so that said apparatus can pass through bends in said piping.

15. The apparatus as recited in 12, wherein said outer surface is made of a material selected from the group consisting of polyvinyl chloride and polytetrafluoroethylene.

16. The apparatus as recited in claim 12, further comprising means carried by said body for supplying power to said apparatus.

17. The apparatus as recited in claim 12, wherein said inspection instrument further comprises:
   a driver coil carried by said body for generating signals that can permeate said piping;
   a detector coil carried by said body for collecting said signals, said signals containing indications of flaws in said piping; and
   means disposed within said body and in electrical communication with said detector coil for storing said signals collected by said detector coil.

* * * * *